US009861432B2

(12) United States Patent
Gittard et al.

(10) Patent No.: US 9,861,432 B2
(45) Date of Patent: Jan. 9, 2018

(54) ROTATION MECHANISM FOR BIPOLAR AND MONOPOLAR DEVICES

(71) Applicant: Cook Medical Technologies LLC, Bloomington, IN (US)

(72) Inventors: Shaun D. Gittard, Winston-Salem, NC (US); Jillian Haac, Winston-Salem, NC (US); Kenneth C. Kennedy, II, Clemmons, NC (US)

(73) Assignee: Cook Medical Technologies, LLC, Bloomington, IN (US)

( * ) Notice: Subject to any disclaimer, the term of this patent is extended or adjusted under 35 U.S.C. 154(b) by 747 days.

(21) Appl. No.: 14/204,087

(22) Filed: Mar. 11, 2014

(65) Prior Publication Data

US 2014/0276808 A1    Sep. 18, 2014

Related U.S. Application Data

(60) Provisional application No. 61/779,986, filed on Mar. 13, 2013.

(51) Int. Cl.
*A61B 18/14*    (2006.01)
*A61B 18/00*    (2006.01)

(52) U.S. Cl.
CPC  *A61B 18/1492* (2013.01); *A61B 2018/00172* (2013.01); *A61B 2018/00178* (2013.01);
(Continued)

(58) Field of Classification Search
CPC . A61B 18/1492; A61B 18/14; A61B 18/1402; A61B 18/149; A61B 2018/1467;
(Continued)

(56) References Cited

U.S. PATENT DOCUMENTS 4,311,143 A  *  1/1982  Komiya ............... A61B 18/14
                                                  606/47
4,753,600 A     6/1988  Williams
(Continued)

FOREIGN PATENT DOCUMENTS

EP        1 864 621 A1    12/2007
JP      2008 253541 A     10/2008
(Continued)

OTHER PUBLICATIONS

International Search Report dated May 28, 2014 for International Application No. PCT/US2014/017561.

*Primary Examiner* — Thomas Giuliani
(74) *Attorney, Agent, or Firm* — Brinks Gilson & Lione

(57) ABSTRACT

An electrosurgical device and a method of orienting the electrosurgical device are provided. The device includes a rotation mechanism including a first and a second connector where the first connector is rotatable relative to the second connector. The device also includes a handle operably connected to the first connector; and a catheter operably connected to the second connector where the handle is rotatable relative to the catheter. The device further includes a first wire having a distal portion anchored to a distal portion of the catheter so that the distal portion of the wire is orientable by rotation of the handle relative to the catheter. At least one of the rotation mechanism or a proximal portion of the wire forms a conductive connection that operably connects a power source to the distal portion of the first wire to energize the distal portion of the first wire in the electrosurgical device.

15 Claims, 8 Drawing Sheets

(52) U.S. Cl.
CPC ............... *A61B 2018/00202* (2013.01); *A61B 2018/00553* (2013.01); *A61B 2018/00601* (2013.01); *A61B 2018/144* (2013.01)

(58) Field of Classification Search
CPC ........... A61B 2018/00178; A61B 2018/00202; A61B 2018/00553; A61B 2018/00601; A61B 2018/00172; A61B 2018/144; A61B 2018/141; A61B 2018/1407
USPC .................................. 606/39, 41, 45, 46, 48
See application file for complete search history.

(56) References Cited

U.S. PATENT DOCUMENTS

| | | | |
|---|---|---|---|
| 4,958,642 A | 9/1990 | Christian et al. | |
| 5,026,371 A * | 6/1991 | Rydell | A61B 18/14 606/113 |
| 5,178,159 A | 1/1993 | Christian et al. | |
| 5,609,573 A | 3/1997 | Sandock | |
| 5,984,920 A * | 11/1999 | Steinbach | A61B 18/14 606/45 |
| 6,074,386 A | 6/2000 | Goble et al. | |
| 6,235,026 B1 | 5/2001 | Smith | |
| 7,449,022 B2 | 11/2008 | Quick et al. | |
| 7,530,953 B2 | 5/2009 | Harshman et al. | |
| 7,717,932 B2 | 5/2010 | McFarlin et al. | |
| 8,172,627 B2 | 5/2012 | Gleason et al. | |
| 2005/0261675 A1 | 11/2005 | Shibata | |
| 2006/0161136 A1* | 7/2006 | Anderson | A61B 90/57 606/1 |
| 2007/0100337 A1* | 5/2007 | Kawahara | A61B 18/1492 606/46 |
| 2009/0306658 A1* | 12/2009 | Nobis | A61B 17/320016 606/46 |
| 2010/0160911 A1 | 6/2010 | Ducharme | |
| 2011/0098601 A1 | 4/2011 | Huynh et al. | |
| 2014/0180280 A1* | 6/2014 | Sigmon, Jr. | A61B 18/18 606/45 |

FOREIGN PATENT DOCUMENTS

WO  WO 2007/149263 A1  12/2007
WO  WO 2008/033929 A2  3/2008

* cited by examiner

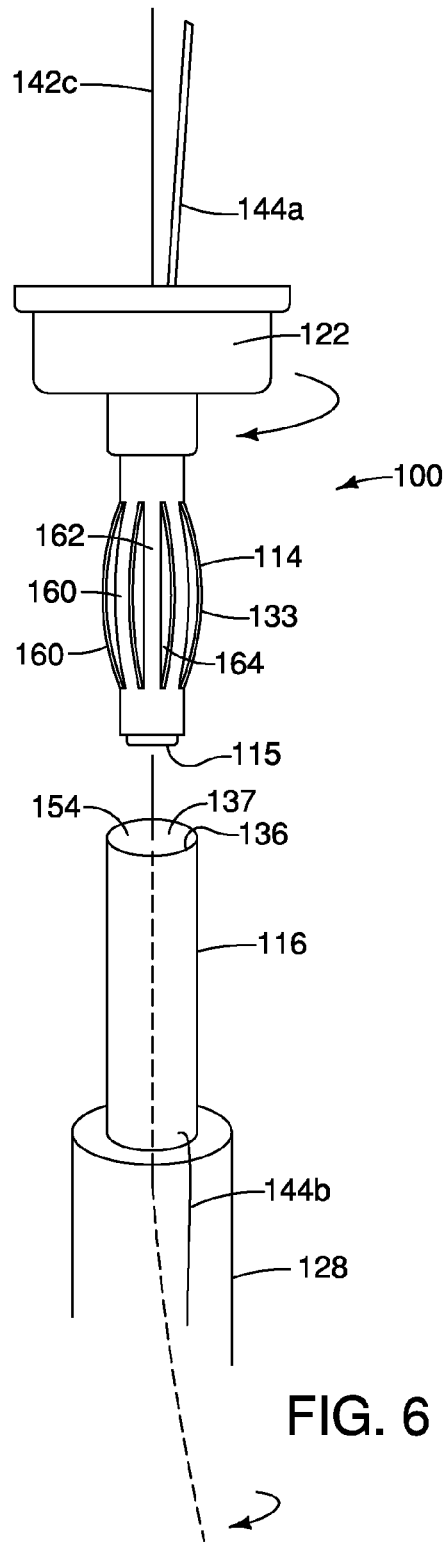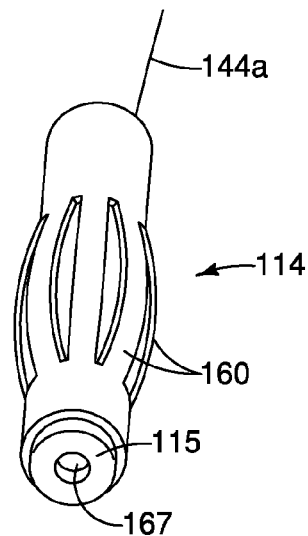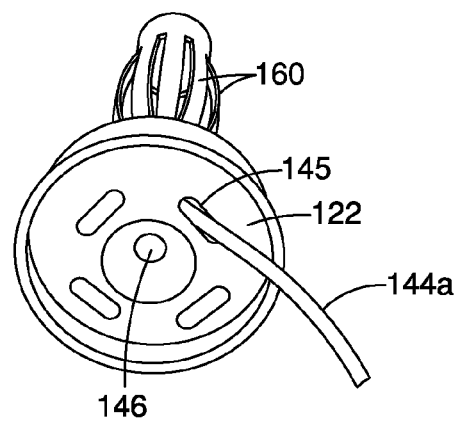
FIG. 6
FIG. 7
FIG. 8

ROTATION MECHANISM FOR BIPOLAR AND MONOPOLAR DEVICES

CROSS-REFERENCE TO RELATED APPLICATIONS

This application claims the benefit under 35 U.S.C. § 119 of U.S. Patent Application No. Ser. No. 61/779,986 filed Mar. 13, 2013; which is incorporated by reference in its entirety.

BACKGROUND

The present devices relate to medical devices, and in particular to electrosurgical devices having a conductive component such as a bipolar or monopolar device.

In endoscopic, or other minimally invasive surgery, generically referred to herein as endoscopic surgery, a sphincterotome may be used in conjunction with an endoscope to provide surgical cutting inside a patient. Specifically, a sphincterotome is used during certain procedures to make an incision in a sphincter. For example, a common treatment of cholecystitis includes the removal of gallstones from the common bile duct. This is frequently done endoscopically with the use of a duodenoscope. The common bile duct proceeds from the junction of the common hepatic duct with the cystic duct, which is open to the gall bladder, and merges with the pancreatic duct, forming the ampulla of Vater, which itself opens into the duodenum at the papilla of Vater. The sphincter of Oddi is a muscular ring that controls passage of fluid from the ampulla of Vater into the duodenum. For removal of gallstones in an endoscopic procedure, access to the common bile duct for removal of gallstones is eased using a sphincterotome to incise or sever the sphincter of Oddi. The sphincterotome is introduced through the duodenoscope and guided through the duodenum to the common bile duct. Once the sphincterotome is guided into the sphincter, its cutting element, commonly a cutting wire, is used to incise the sphincter, and thereby improve access to the bile duct and impacted gallstones.

Another example of a common procedure utilizing a sphincterotome is endoscopic retrograde cholangiopancreatography (ERCP), a diagnostic visualization technique used for a variety of clinical applications. In this procedure, a contrast fluid such as a radio-opaque dye is introduced through a tube into the ampulla of Vater. A sphincterotome is often employed to provide access through the sphincter of Oddi. ERCP is often used in diagnosis of cholecystitis, as well as in the diagnosis and treatment of other conditions of the pancreatic and common bile ducts and related structures.

One problem associated with the use of a cutting wire on a sphincterotome or other device is that the cutting wire is difficult to orient for cannulation and cutting of the sphincter. The correct orientation of the cutting wire relative to the sphincter is important for proper cutting of the sphincter to provide access through the sphincter. In addition, the sphinctertome or other device may be used to navigate into smaller branches of the ductal system where rotation of the cutting wire may be necessary to provide access to the desired ducts. Rotation of the cutting wire may be difficult due twisting of the wire relative to other features of the device. For example, in a bipolar device, the cutting wire when rotated may cross over the return wire.

What is needed in the art is a sphincterotome that is rotatable to properly orient the cutting wire anchored to the distal portion of the sphincterotome relative to the tissue. The cutting wire should be rotatable without interference from other portions of the device.

BRIEF SUMMARY

Accordingly, it is an object of the present invention to provide a device and a method having features that resolve or improve on one or more of the above-described drawbacks.

In one aspect, an electrosurgical device including a rotation mechanism is provided. The electrosurgical device includes a rotation mechanism including a first connector; and a second connector where the first connector is rotatable relative to the second connector. The electrosurgical device also includes a handle operably connected to the first connector; and a catheter operably connected to the second connector where the handle is rotatable relative to the catheter. The electrosurgical device further includes a first wire having a distal portion anchored to a distal portion of the catheter so that the distal portion of the wire is orientable by rotation of the handle relative to the catheter. At least one of the rotation mechanism or a proximal portion of the wire forms a conductive connection that operably connects a power source to the distal portion of the first wire to energize the distal portion of the first wire in the electrosurgical device.

In another aspect, an electrosurgical device including a rotation mechanism is provided. The rotation mechanism includes a first connector including a conducting region and a second connector including a conducting region. The first connector is rotatable relative to the second connector and the second connector forming a rotatable conductive connection to the first connector to form a second electrode of the electrosurgical device. The electrosurgical device also includes a handle operably connected to the first connector, a catheter operably connected to the second connector where the handle is rotatable relative to the catheter and a first wire operably connected to the handle and the catheter. The wire is electrically isolated from the first connector and the second connector and the wire is a first electrode.

In another aspect, a method of orienting a distal portion of a wire of an electrosurgical device is provided. The method includes operably connecting a proximal portion of the wire to a handle of the electrosurgical device, anchoring the distal portion of the wire to a distal portion of a catheter of the electrosurgical device, connecting a first connector having a conducting region to the handle and connecting a second connector having a conducting region to the catheter so that the first connector rotates relative to the second connector to form a rotatable conducting section of the electrosurgical device. A proximal portion of the wire forming a conductive connection that operably connects a power source to the distal portion of the wire to energize the distal portion of the wire, the wire comprising a first electrode and the rotatable conducting second comprising a second electrode. The method further includes rotating the handle to orient the distal portion of the wire while hold a proximal portion of the catheter in position.

BRIEF DESCRIPTION OF THE DRAWINGS

FIG. 1 is a sectional view of a rotation mechanism for an electrosurgical device in accordance with an embodiment of the present invention;

FIG. 2 is side elevational view of an electrosurgical device including a rotation mechanism in accordance with an embodiment of the present invention;

FIG. 6 is an exploded view of a rotation mechanism in accordance with an embodiment of the present invention;

FIG. 7 is a perspective view of the first connector of the rotation mechanism shown in FIG. 6;

FIG. 8 is a perspective view of the first connector and a hub of the rotation mechanism shown in FIG. 6;

DETAILED DESCRIPTION

Figure 1:
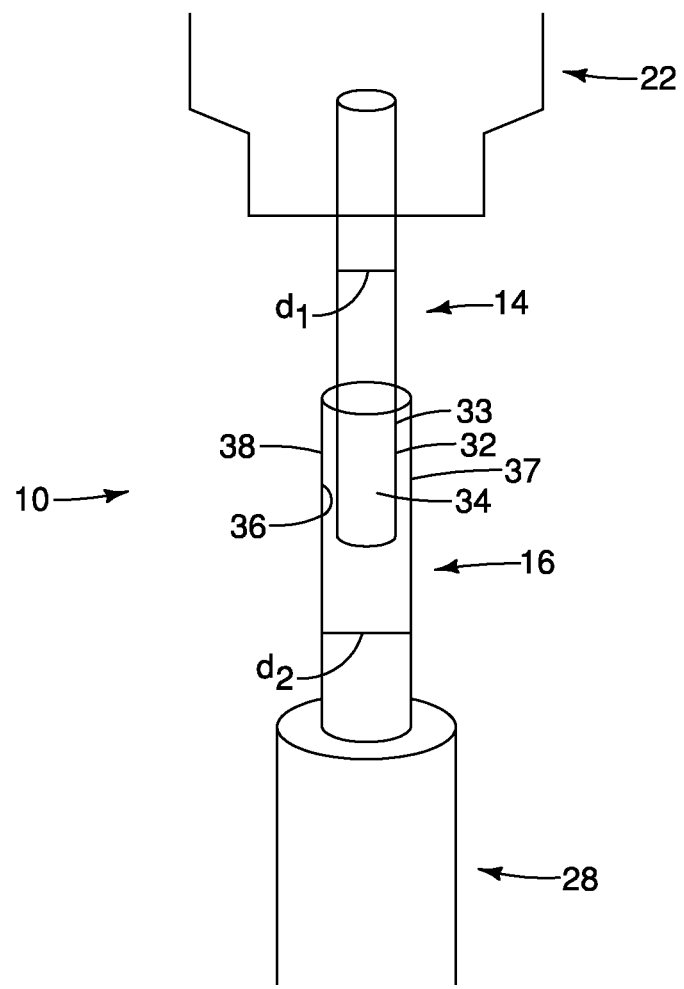

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the device to a patient. Hence the term "distal" means the portion of the device that is farthest from the physician and the term "proximal" means the portion of the device that is nearest to the physician.

Figure 2:
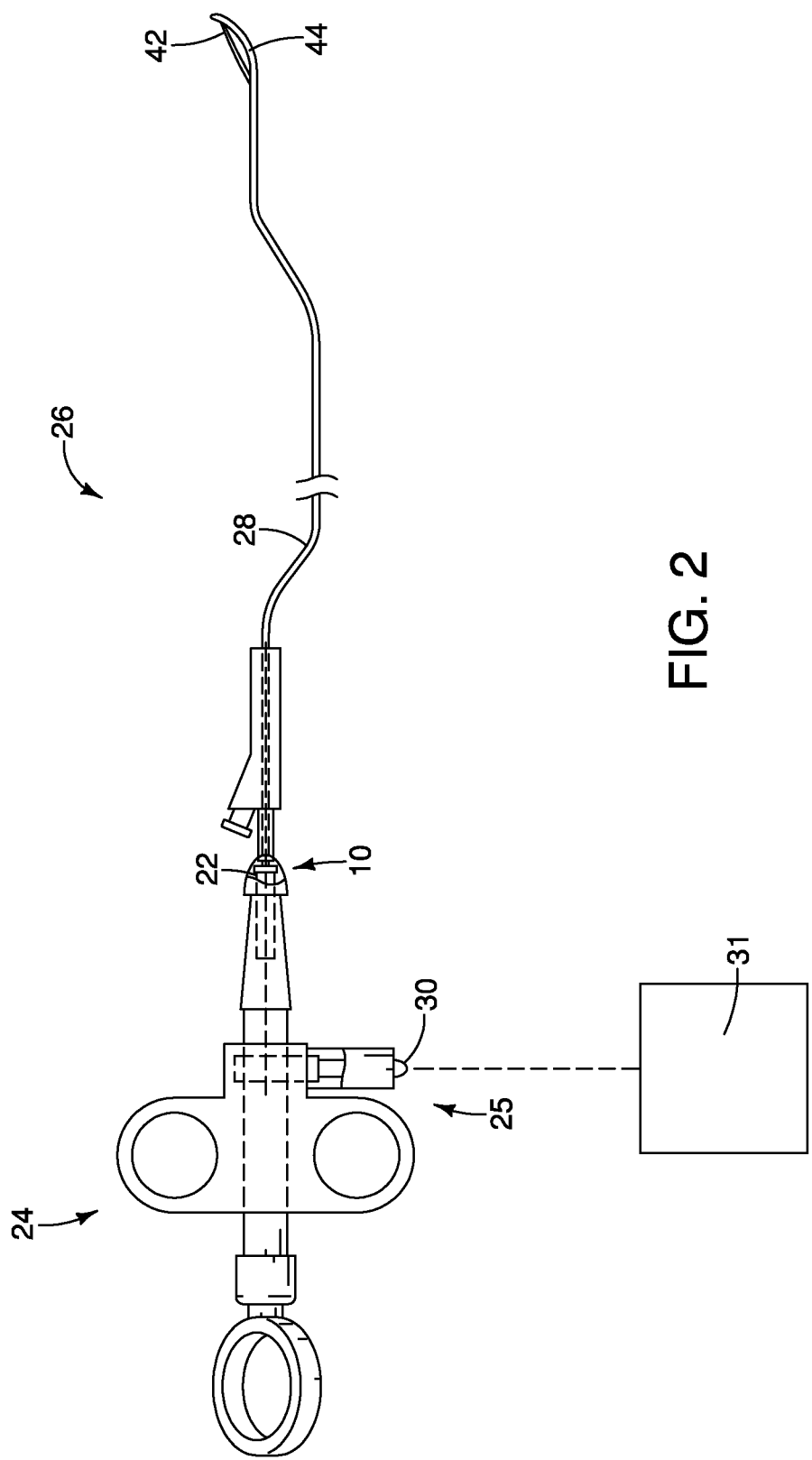

FIG. 1 illustrates an embodiment of a rotation mechanism 10 for use with an electrosurgical device in accordance with the present invention. The rotation mechanism can be controlled by providing a frictional force to overcome in order for the user to be able to rotate the rotation mechanism. The amount of friction can be optimized to allow the user to rotate the rotation mechanism yet sufficient to prevent inadvertent rotation. The control of the rotation mechanism is described in more detail below. The rotation mechanism 10 includes a first connector 14 and a second connector 16 that are rotatable relative to each other. As shown in FIG. 1, the first connector 14 and the second connector 16 may be provided as tubular cannulae that are sized and shaped so that one of the first or second connectors 14, 16 fits inside the other of the first or second connectors 14, 16. As shown in FIG. 1, the first connector 14 has a slightly smaller diameter $d_1$ so the first connector 14 fits into the second connector 16 having a diameter $d_2$. The first and second connectors 14, 16 are sized and shaped so that the first and second connectors 14, 16 can smoothly rotate relative to each other and in some embodiments may also maintain contact at all times. The length of the first and second connectors 14, 16 and the amount of overlap of the first and second connectors 14, 16 may be varied to optimize the surface contact between the members 14, 16. In some embodiments, the overlap between the first and second connector may be about 1 mm to about 5 cm. As shown in FIG. 1, the first connector 14 may be operably connected to a hub 22 of a handle 24 of an electrosurgical device 26. FIG. 2 illustrates an exemplary electrosurgical device 26 having the handle 24 at a proximal portion 25 of the electrosurgical device 26. As shown in FIG. 1, the second connector 16 may be operably connected to a catheter 28 of the electrosurgical device 26. In some embodiments, the first connector 14 may have the larger diameter $d_2$ and the second connector 16 may have the smaller diameter $d_1$ so that the second connector 16 fits within the first connector 14. (See FIG. 5.) The first connector 14 and the handle 24 are rotatable relative to the second connector 16 and the catheter 28.

In some embodiments, the first and second connectors 14, 16 maintain contact at all times so that an energy, such as but not limited to RF energy, may be conducted between a conducting region 33 of the first connector 14 and conducting region 37 of the second connector 16. In some embodiments, the entire first and second connectors 14, 16 may be formed from an electrically conductive material to form the conducting regions 33, 37. In some embodiments, portions of the first and second connectors 14, 16 may be coated with an insulating material so that conducting regions 33, 37 are positioned to contact each other. In some embodiments, the first connector 14 may have an outer surface region 32 that is conductive at a distal end portion 34 of the first connector 14. The second connector 18 may have an inner surface region 36 that is conductive at a proximal end portion 38 of the second member 18 when the first connector 14 fits within the second connector 16 so that the inner and outer conductive surfaces 32, 34 overlap and contact each other and form a conductive portion 21. In some embodiments, a nominal resistance of up to about 10 Ohms may be provided. In some embodiments, the first and second connectors 14, 16 or one of the first and second connectors 14, 16 may be made of a non-conductive material. Where one or more of the connectors 14, 16 is made of non-conductive material or in addition to a connector that is made of conductive material, an additional material may be provided that is conductive or as an alternative to the first and second connectors 14, 16. By way of non-limiting example, the conductive regions may be formed of metal strips or sheets, wires, coils, springs, conducting polymers, conducting inks, combinations thereof and the like. In some embodiments, the conductive materials may include stainless steel, steel, tungsten, copper, brass silver, gold, aluminum, zinc, nickel, bronze, iron, platinum and the like. An exemplary alternative conductor is shown below in FIG. 6 as a banana-type connector.

In some embodiments, the rotation mechanism 10 may be used with a monopolar electrosurgical device so that the first and second connectors 14, 16 form the conductive connection for a cutting wire 42. As shown in FIG. 2, the cutting wire includes an exposed portion 42e at a distal end portion 44 of the electrosurgical device 26 shown in FIG. 2. The cutting wire 42 is anchored at the distal end portion 44 and the exposed portion 42e is used to cut the tissue. The cutting wire 42 extends from the distal end portion 44 and is operatively connected to the handle 24 of the electrosurgical device 26 which is connected to a power supply or electrosurgical unit 31 through a connector hub 30 on the handle 24. The rotation mechanism 10 shown in FIG. 1 allows the first and second connectors 14, 16 to rotate relative to each other so that the handle 24 rotates the cutting wire 42 relative to the catheter 28 so that the exposed portion 42e of the cutting wire 42 at the distal end portion 44 of the electrosurgical device 26 can be rotatably positioned so that the exposed portion 42e of the cutting wire 42 is orientable for cannulation and cutting at a tissue site. Since the cutting wire 42 is anchored at the distal portion 44 of the catheter 28, the distal portion 44 of the catheter 28 is moved with the cutting wire 42 while the remainder of the catheter 28 and the second connector 16 are not moved by the rotation of the handle 24.

Figure 3:
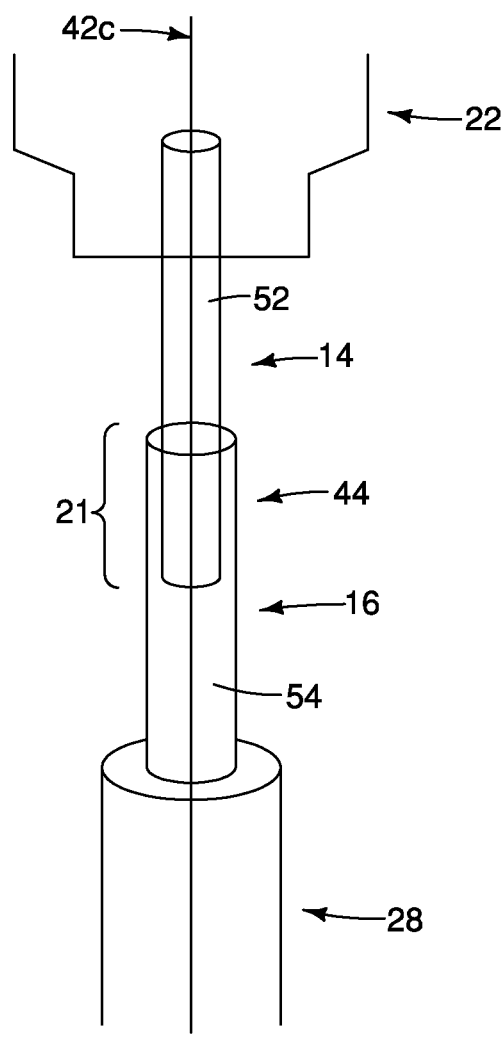
FIG. 3 is a sectional view of a rotation mechanism for an electrosurgical device in accordance with an embodiment of the present invention.

In some embodiments where the electrosurgical device 26 is a monopolar device, a single wire 42c may extend from the proximal portion 25 of the handle 24 through the hub 22 to the distal end portion 44 of the electrosurgical device 26 so that the exposed end 42e of the single wire 42c is exposed for cutting the tissue at the appropriate site. The cutting wire 42c may extend through a lumen 52 of the first connector 14 and through a lumen 54 of the second connector 16 as shown in FIG. 3. The cutting wire 42c extends through the catheter 28 to the distal end portion 44 of the electrosurgical device 26. Since the cutting wire 42c is positioned within the lumens 52, 54 of the first and second connectors 14, 16, the connectors 14, 16 may be rotated relative to each other by rotating the handle 24 relative to the catheter 28 to position the exposed cutting portion 42e in the proper orientation without crossing the cutting wire 42c with any part of the electrosurgical device 26. With a monopolar device as shown in FIG. 3, the first and second connectors 14, 16 do not need to be conductive. The cutting wire 42c may be insulated where the cutting wire extends through the electrosurgical device 26 until the wire 42 is exposed at the distal end portion 44. The exposed cutting portion 42e is free from insulation.

Figure 4:
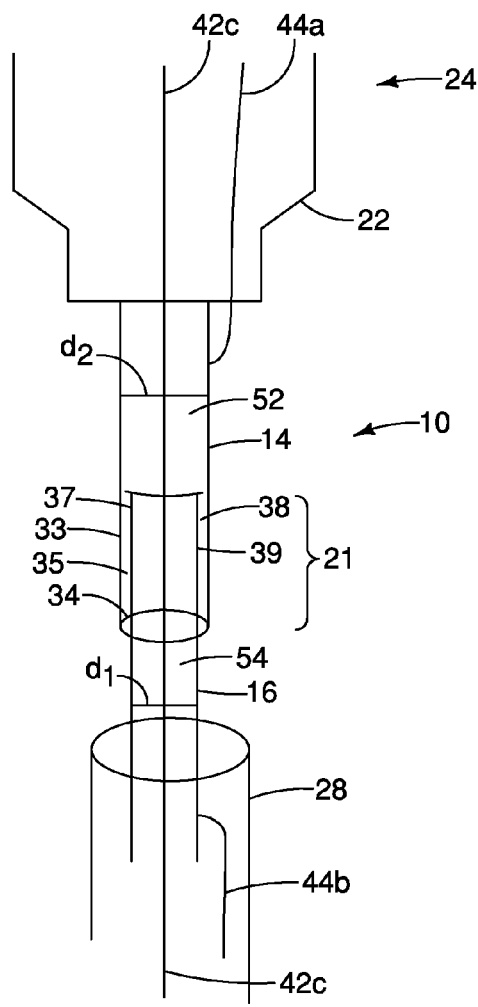
FIG. 4 is a sectional view of a rotation mechanism for a bipolar electrosurgical device in accordance with an embodiment of the present invention.

The rotation mechanism 10 may also be used with a bipolar device having an active and a return wire. An exemplary bipolar configuration is shown in FIG. 4. FIG. 4 also illustrates the first connector 14 having the larger diameter $d_2$ than the second connector 16 having the smaller diameter $d_1$ so that the second connector 16 fits within the first connector 14. The first and second connectors 14, 16 as shown in FIG. 4 are configured to maintain contact at all times so that an energy, such as but not limited to RF energy, may be conducted between the first and second connectors 14, 16. In some embodiments, the entire first and second connectors 14, 16 may be formed from an electrically conductive material. In some embodiments, portions of the first and second conductive members 14, 16 may be coated with an insulating material so that conductive portions are positioned to contact each other. In some embodiments, the first connector 14 may have an inner surface 35 that is conductive at the distal end portion 34 of the first connector 14. The second connector 16 may have an outer surface 39 that is conductive at the proximal end portion 38 of the second member 18. The first connector 14 fits over the second connector 16 so that the inner and outer conductive surfaces 39, 35 overlap and contact each other to provide the conductive portion 21. The bipolar configuration for the rotation mechanism 10 may also have the first connector 14 having the smaller diameter $d_1$ and the second connector 16 having the larger diameter $d_2$ so that the first connector 14 fits within the second connector 16 as described above with reference to FIG. 1. By way of non-limiting example, the conductive portion may be formed of metal strips or sheets, wires, coils, springs, conducting polymers, conducting inks, combinations thereof and the like.

As shown in FIG. 4, the bipolar device includes the cutting wire 42c that connects to the handle 24 and extends to the distal end portion 44 of the catheter 28 so that the exposed cutting portion 42e of the cutting wire 42c forms the active electrode that is orientable to cut the tissue. The cutting wire 42c extends through the lumen 52 of the first connector 14 and through the lumen 54 of the second connector 16. The cutting wire 42c extends through the catheter 28 to the distal end portion 44 where the cutting wire 42c is anchored and the cutting portion 42e is exposed. In some embodiments, the cutting wire 42c may be insulated except for the exposed portion 42e so that the cutting wire 42c does not contact the first and second connectors.

A return wire 44 for the bipolar device is shown in FIG. 4 where the return wire includes a proximal wire 44a that is connected to the first connector 14 and a distal wire 44b that is connected to the second connector 16. The proximal and distal return wires 44a, 44b are electrically connected via the conductive portion 21 formed by the connection of the first and second connectors 14, 16. The distal wire 44b may extend to the distal end portion 44 to act as the return wire for the cutting wire 42c. The first connector 14 connected to the handle 24 and the second connector 16 connected to the catheter 28 are freely rotatable relative to each other. In this configuration, the cutting wire 42c and the return wires 44a, 44b do not cross each other so the cutting wire 42c can be rotated in any direction and to any degree to orient the exposed portion 42e for cutting the tissue and cannnulating the papilla. In some embodiments, the first and/or second connectors 14, 16 may form the return electrode 44 without including one or both of the proximal return wire 44a and the distal return wire 44b.

Figure 5:
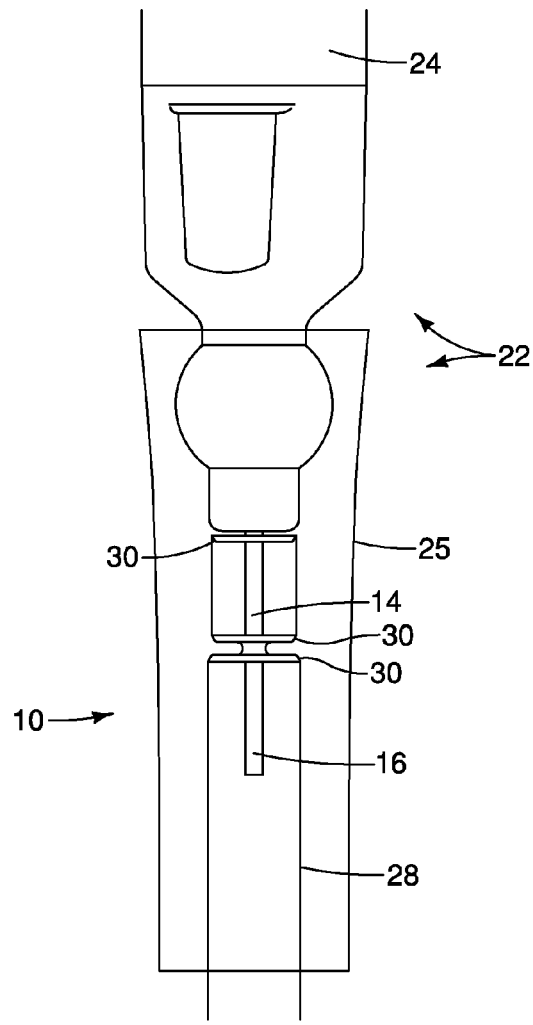
FIG. 5 is a sectional view of a rotation mechanism within a housing in accordance with an embodiment of the present invention.

FIG. 5 illustrates the rotation mechanism 10 within a housing 25. The housing 25 may be configured to hold the first connector 14 and the second connector 16 together so that a longitudinal position of the first and second connectors 14, 16 is substantially fixed and allows the first and second connectors 14, 16 to rotate relative to each other. In some embodiments, a plurality of rings 30, such as o-rings, may be used to make a friction fit for the first and second connectors 14, 16 within the housing 25. The rings 30 prevent inadvertent rotation of the first and second connectors 14, 16 yet allow the user to overcome the frictional forces provided by the rings 30 when rotation is desired. As shown in FIG. 5, at least one ring 30 is provided around each of the first and second connectors 14, 16. Additional rings 30 may also be provided to increase the amount of frictional force needed to be overcome to rotate the first and second connectors 14, 16 relative to each other. The hub 22 may be provided as a ball and socket connection that connects the first connector 14 to the handle 24. In some embodiments, the housing 25 may be injection molded although other methods for forming the housing are also possible.

An alternative embodiment of a bipolar configuration of a rotation mechanism 100 is shown in FIG. 6. First and second connectors 114, 116 as shown in FIG. 6 are configured to maintain contact so that an energy, such as but not limited to RF energy, may be conducted between the first and second connectors 114, 116. The first and second connectors 114, 116 are similar to the first and second connectors described above and may include features similar to the first and second connectors 114, 116 described above however, the configuration of the first connector 114 is different. The first connector 114 shown in FIG. 6 may be provided as a banana-type connector. The first connector 114 includes one or more resilient arms 160 that bow outward from a center longitudinal axis 162 of the first connector 114. The amount of curve of the arms 160 can control the amount of force needed to rotate the first connector 114 relative to the second connector 116 and can also improve the electrical connection between the first and second connectors 114, 116. Other forms of connector in addition to the banana-type connector that include one or more resilient arms may also be used where at least one arm forms a connection with the second connector. The first connector 114 is shown connected to a hub 122 that connects to the handle 124 of the electrosurgical device 126. A tubular member 115 may extend through an inner portion 164 of the first connector 114. In some embodiments, the tubular member 115 may be made from an insulating material and include a lumen 167 extending therethrough to accommodate a cutting/active wire 142c extending through the lumen 167 as shown in FIG. 7. FIG. 8 illustrates a top perspective view of the hub 122 connected to the first connector 114 and showing a proximal return wire 144a extending proximally through an offset opening 145. As shown in FIG. 8, the proximal return wire 144a is offset from a center opening 146 that connects to the lumen 160 of the tubular member 115 and through which the cutting wire 142c extends. In some embodiments, the proximal return wire 144a may be centrally positioned and the cutting wire 142c may be offset from the center opening 146. The hub 122 keeps the cutting wire 142c away from the proximal return wire 144a. In some embodiments, the first connector 114 may not include the proximal return wire 144a to complete the return electrode 144 and may be directly connected to the power source. The second connector 116 may be connected to a distal return wire 144b in the catheter 28.

As shown in FIG. 6, the second connector 116 is sized and shaped to fit over the first connector 114 and to contact the resilient arms 160. At least a portion of the first connector 114 is formed of a conductive material so that when the second connector 116 is advanced over the first connector 114, the resilient arms 160 contact an inner surface 136 of the second connector 116 to form a conductive portion 121 (see FIG. 9). In some embodiments, the second connector 116 may be provided as a banana-type connector or other type connector having one or more resilient arms and the first connector 114 may be provided as a tubular member that fits over the second connector 116.

As shown in FIG. 6, the bipolar device includes the cutting wire 142c that connects to the handle 124 of the electrosurgical device 126 shown in FIG. 6 and extends to the distal end portion 144 of the catheter 128 so that the exposed cutting portion 142e of the cutting wire 142c forms the active electrode that is orientable to cut the tissue. The cutting wire 142c extends through the lumen 160 of the tubular member 115 within the first connector 114 and through a lumen 154 of the second connector 116. The cutting wire 142c extends through the catheter 128 to the distal end portion 144 where the cutting wire 142c is anchored. The handle 124 may be rotated to rotate the cutting wire 142c to orient the exposed portion 142e for cutting and the distal portion 144 of the device for cannulation.

A return wire 144 for the bipolar device is shown in FIG. 6 where the return wire includes a proximal return wire 144a that is connected to the first connector 114 and a distal return wire 144b that is connected to the second connector 116. The proximal and distal return wires 144a, 144b are electrically connected via the conductive portion 121 formed by the connection of the first and second connectors 114, 116. The distal wire 144b may extend to the distal end portion 144 of the catheter 128 to act as the return wire for the cutting wire 142c. The first connector 114 connected to the handle 124 and the second connector 116 connected to the catheter 128 are freely rotatable relative to each other. The arms 160 of the first connector 114 help to maintain the electrical connection between the first connector 114 and the second connector 116 and still allow the first and second connectors 114, 116 to rotate relative to each other. In this configuration, the cutting wire 142c and the return wires 144a, 144b do not cross each other so the cutting wire 142c can be rotated in any direction and to any degree to orient the exposed portion 142e for cutting the tissue. The wires 144a, 144b together with the conductive portion 121 of the first and second connectors 114, 116 form the return electrode 144.

Figure 9:
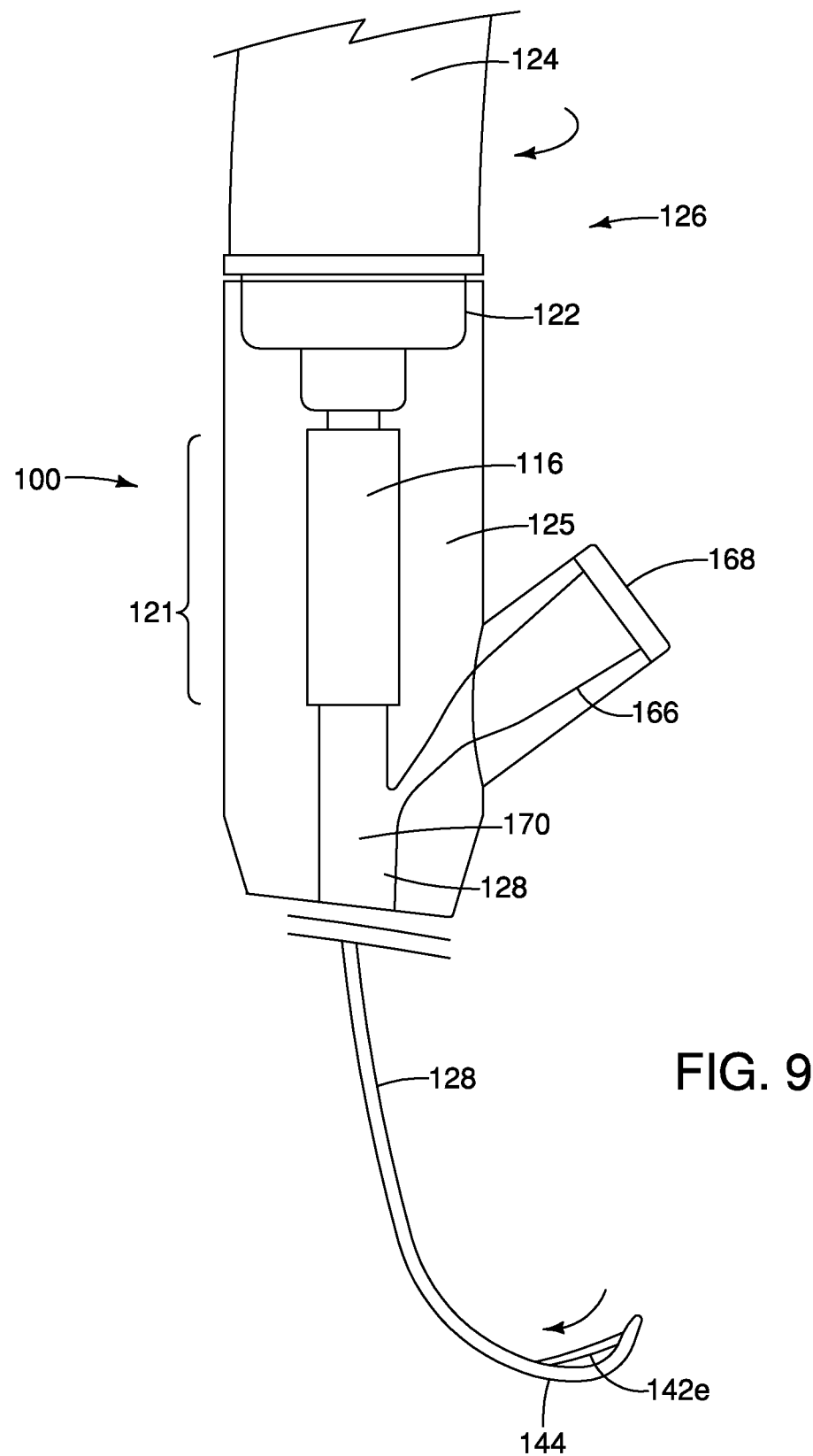
FIG. 9 is a sectional view of a rotation mechanism within a housing in accordance with an embodiment of the present invention.

FIG. 9 illustrates the rotation mechanism 100 with the first and second connectors 114, 116 connected and positioned within a housing 125. The second connector 116 is positioned over the first connector 114 and the first and second connectors 114, 116 are held substantially longitudinally fixed relative to each other within the housing 125. The first connector 114 is rotatable within the housing and the second connector 116 by rotation of the handle 124. In some embodiments, the housing 125 may include a port 166 that is positioned distal to the rotation mechanism 100. The port 166 includes a lumen 168 that connects to a lumen 170 of the catheter 128.

Figure 10A:
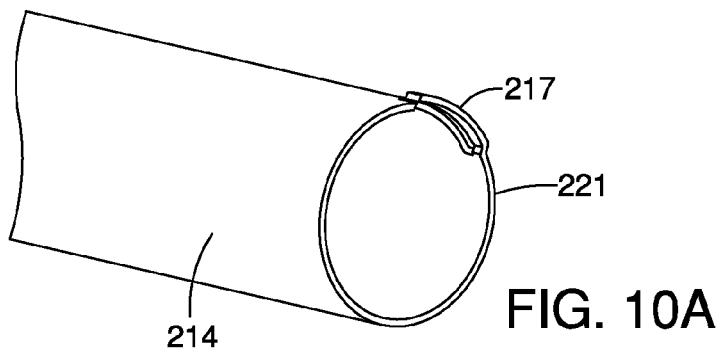
FIGS. 10A-10C are partial perspective view of a first connector in accordance with an embodiment of the present invention.
Figure 10B:
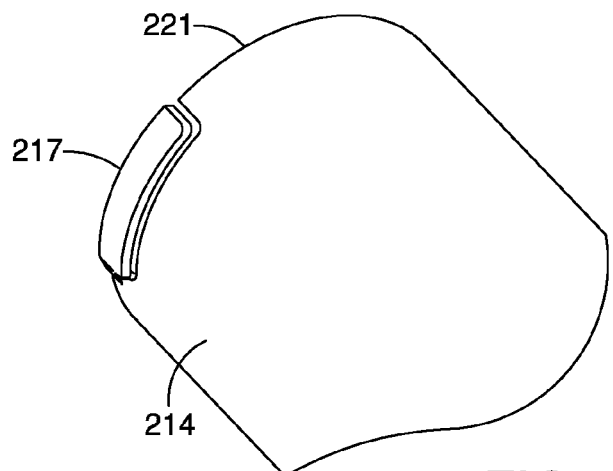
Figure 10C:
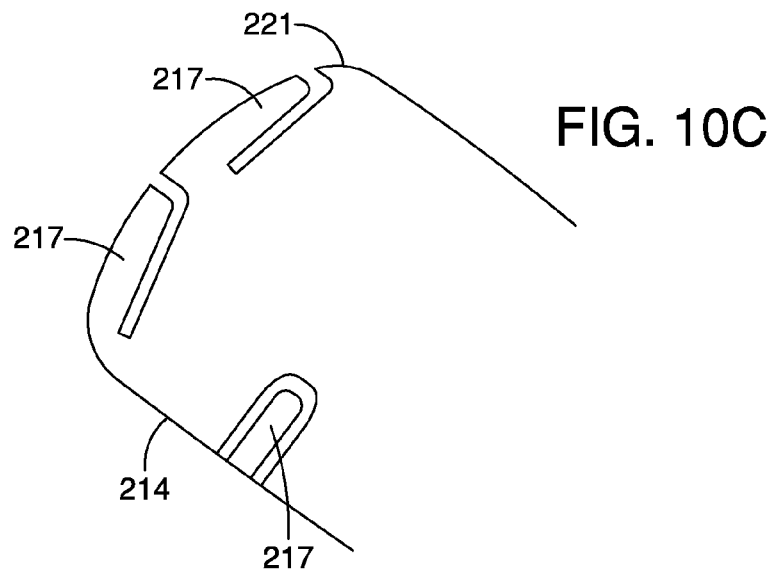

FIGS. 10A-10C illustrate an alternative embodiment of a first connecting member 214. The first connecting member 214 may be used in combination with the second connectors 16, 116 described above and may include any of the features described above. As shown in FIGS. 10A and 10B, the first connector may include one or more spring-like leaves 217 to form the electrical connection with the second connector 16, 116. FIG. 10C shows an embodiment having two spring-like leaves 217 on an end 221 of the first connector 214. The spring-like leaves 217 may be formed by partially separating a portion from the main body and reshaping the portion as a leaf shape having an outer diameter 223 that is larger than the inner diameter of the second connector 16, 116 so that the leaf 217 forms the electrical connection between the first and second connectors 214, 16, 116. The leaf 217 is resilient and can be moved inward to allow the second connector 16, 116 to be positioned over the leaf 217. The leaf 217 is resilient to provide and maintain the conductive connection to the second member 16, 116 and to also provide some frictional resistance to avoid inadvertent rotation. As shown in FIG. 10C, the spring-like leaf 217 may also be formed at any position on the first connector 214. Any number of leaves 217 may be included. The leaves 217 may have any shape and configuration that provides a connection between the first connector 214 and the second connector 16, 116. The leaves may be formed by laser cutting, stamping and the like. In some embodiments, the leaves 217 may be made as separately and joined to the first connector 214 by welding, soldering, riveting or other joining methods know to one skilled in the art. In some embodiments, the second connector may include one or more leaves that project inward toward the first connector and in some embodiments, both the first and second connectors may include leaves.

Figure 11A:
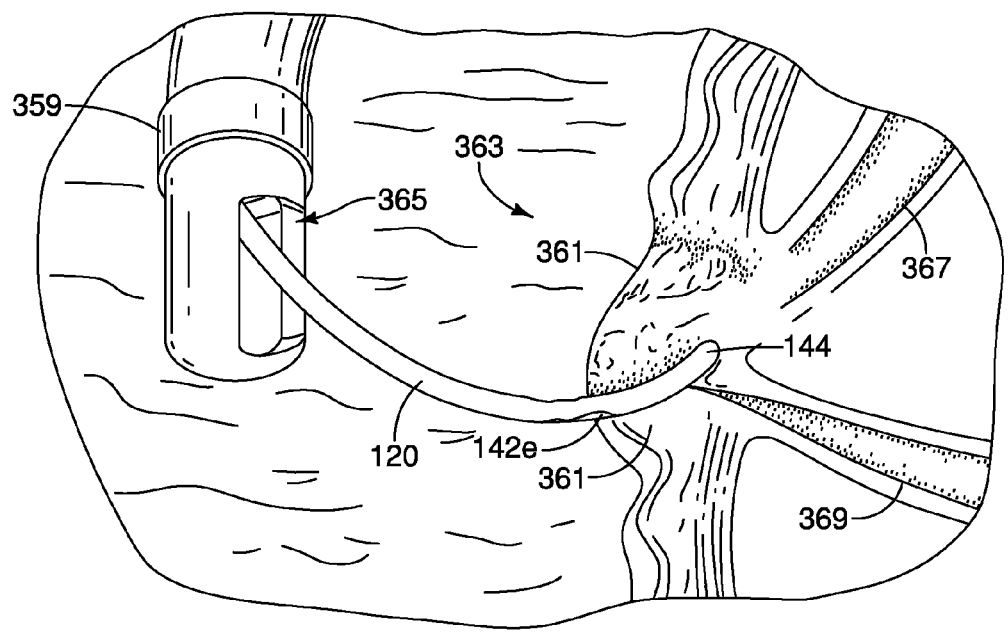
FIGS. 11A and 11B illustrate operation of an electrosurgical device having a rotation mechanism in accordance with the present invention.
Figure 11B:
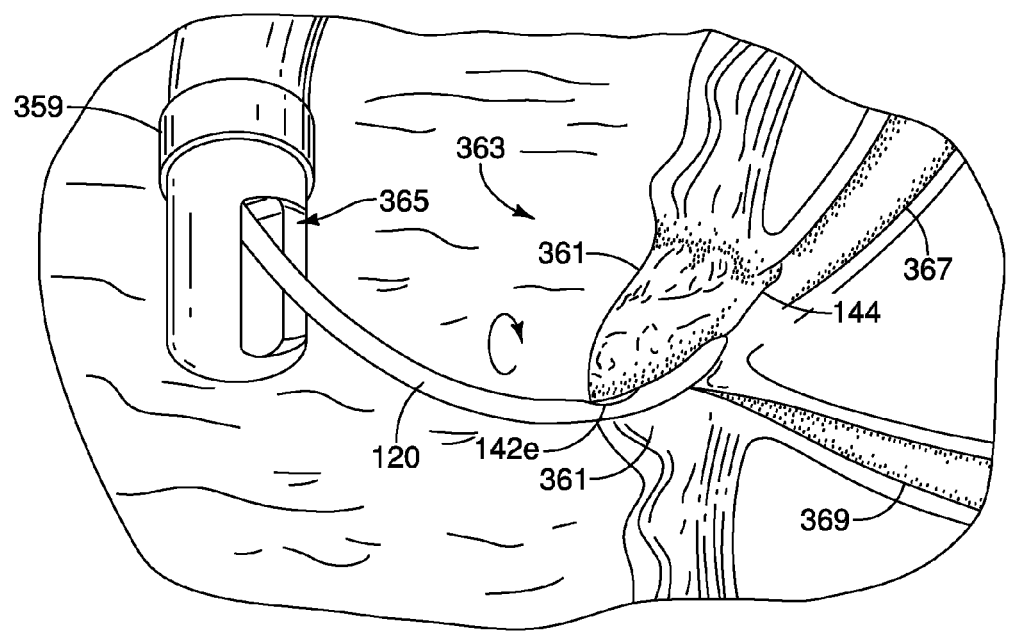

An exemplary procedure utilizing the rotation mechanism 10, 100 as part of a sphincterotome, for example in accessing the biliary system via the Sphincter of Oddi is shown in FIGS. 11A and 11B and is described as follows. An endoscope 359 is advanced into the patient and positioned near the Sphincter of Oddi 361 in the Papilla of Vater 363. The endoscope 359 is positioned to allow viewing of sphincter 361 as is known. The catheter 128 is extended into engagement with sphincter 361 by inserting the distal end portion 144 of the catheter into the Ampulla of Vater, which communicates with the common bile duct 367 and the pancreatic duct 369. The catheter 128 may be rotated using the wire 142 for cannulation of the Papilla 363. The catheter 128 may be extended into the Ampulla of Vater until the cutting wire 142c and the portion to be used for cutting 142e is longitudinally aligned with the stricture to be cannulated. The handle 124 is rotated as indicated by the arrow shown in FIG. 9 to move the cutting wire 142c and the exposed portion 142e into the proper orientation for cutting the tissue. The cutting wire 142c rotates with the handle 124 and the first connector 114 so that the distal portion 144 of the catheter 128 is rotated where the cutting wire 142c is anchored to the distal portion 144. The remainder of the catheter 128 does not rotate. The cutting wire 142c freely rotates and does not cross any other portions of the device. Once the exposed portion 142e is correctly oriented, the cutting wire 142c is energized and the tissue is cut. The return wire 144 maintains the circuit from the distal return wire 144b connected to the second connector 116 which is conductively connected to the first connector 114 that has the proximal return wire 144a connected thereto. If a second cut is needed, requiring a different orientation for the exposed portion 142e of the cutting wire 142c, the handle 124 may be rotated to move the cutting wire 142c so that the exposed portion 142e is in the proper orientation for the second cut. The catheter 128 may also be used to for selective cannulation of branches in the biliary tree where rotation of the distal portion 144 of the catheter 128 is necessary for cannulation of the branches.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. An electrosurgical device comprising:
   a rotation mechanism comprising:
     a first connector; and
     a second connector, the first connector rotatable relative to the second connector;
   a handle operably connected to the first connector;
   a catheter operably connected to the second connector, the handle rotatable relative to the catheter;
   a first wire having a distal portion anchored to a distal portion of the catheter, the distal portion of the wire being orientable by rotation of the handle relative to the catheter; at least one of the rotation mechanism or a proximal portion of the wire forming a conductive connection that operably connects a power source to the distal portion of the first wire to energize the distal portion of the first wire in the electrosurgical device; and
   a return electrode comprising a first portion operably connected to the first connector and a second portion operably connected to the second connector, the first portion free from direct connection to the second portion so that the first wire is orientable without interference from the return electrode.

2. The electrosurgical device according to claim 1, wherein one of the first connector or the second connector comprises one or more resilient arms.

3. The electrosurgical device according to claim 2, wherein the one of the first connector or the second connector comprises a leaf-like projection forming the conductive connection.

4. The electrosurgical device according to claim 1, wherein at least one of the first connector or the second connector comprises a tubular member.

5. The electrosurgical device according to claim 1, wherein the first connector comprises a conducting region and the second connector comprises a conducting region to form a rotatable conduction section of the electrosurgical device.

6. The electrosurgical device according to claim 1, wherein one of the first connector and the second connector fits at least partially over the other of the first connector and the second connector to form a rotatable conductive connection.

7. The electrosurgical device according to claim 1, wherein the first connector is operably connected to the power source.

8. The electrosurgical device according to claim 1, wherein the rotation mechanism is provided within a housing.

9. The electrosurgical device according to claim 8, wherein the housing longitudinally secures the first connector relative to the second connector.

10. The electrosurgical device according to claim 8, wherein the housing comprises an injection port positioned distal to the rotation mechanism.

11. The electrosurgical device according to claim 1, wherein the rotation mechanism further comprises one or more rings surrounding the first connector and/or the second connector to provide a friction between the first and second connectors to control torques required to rotate the handle relative to the catheter.

12. The electrosurgical device according to claim 1, wherein one or more resilient arms of the first or second connector or a leaf-like projection of the first or second connector provides a friction between the first and second connectors to control torques required to rotate the handle relative to the catheter.

13. An electrosurgical device comprising:
   a rotation mechanism comprising:
     a first connector comprising a conducting region; and
     a second connector comprising a conducting region, the first connector rotatable relative to the second connector and the second connector forming a rotatable conductive connection to the first connector;
   a handle operably connected to the first connector;
   a catheter operably connected to the second connector, the handle rotatable relative to the catheter;
   a first wire operably connected to the handle and the catheter, the first wire electrically isolated from the first connector and the second connector, the first wire comprising a first electrode; and
   a second electrode comprising a first portion operably connected to the first connector and a second portion operably connected to the second connector, the first portion free from direct connection to the second portion so that the first wire is orientable without contacting the second electrode.

14. The electrosurgical device according to claim 13, wherein the rotation mechanism further comprises one or more rings surrounding the first connector or the second connector, or one or more resilient arms or leaf-like projections on the first connector or the second connector to provide a friction between the first and second connectors to control torques required to rotate the handle relative to the catheter.

15. The electrosurgical device according to claim 14, wherein the other of the first connector and the second connector comprises a tubular member that fits at least partially over the one or more resilient arms or the leaf-like projections.

* * * * *